United States Patent
Scherr et al.

(10) Patent No.: US 9,681,797 B2
(45) Date of Patent: Jun. 20, 2017

(54) VIDEO ENDOSCOPE AND VIDEO ENDOSCOPE SYSTEM

(71) Applicant: OLYMPUS WINTER & IBE GMBH, Hamburg (DE)

(72) Inventors: Patrick Scherr, Alt-Moelln (DE); Andreas Braun, Kaltennordheim (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 447 days.

(21) Appl. No.: 14/308,852

(22) Filed: Jun. 19, 2014

(65) Prior Publication Data

US 2014/0303439 A1  Oct. 9, 2014

Related U.S. Application Data

(63) Continuation of application No. PCT/EP2012/005137, filed on Dec. 13, 2012.

(30) Foreign Application Priority Data

Dec. 29, 2011  (DE) .................. 10 2011 090 132

(51) Int. Cl.
*A61B 1/06*  (2006.01)
*A61B 1/05*  (2006.01)
(Continued)

(52) U.S. Cl.
CPC ............ *A61B 1/05* (2013.01); *A61B 1/00096* (2013.01); *A61B 1/00105* (2013.01);
(Continued)

(58) Field of Classification Search
USPC .................. 600/109–112, 160–178
See application file for complete search history.

(56) References Cited

U.S. PATENT DOCUMENTS 4,732,156 A    3/1988  Nakamura
5,056,902 A *  10/1991 Chinnock .......... A61B 1/00066
                                                        359/503
(Continued)

FOREIGN PATENT DOCUMENTS

DE    19903437 C1    8/2000
DE    19681437 B4    4/2009
(Continued)

OTHER PUBLICATIONS

International Search Report dated Apr. 22, 2013 issued in PCT/EP2012/005137.
(Continued)

*Primary Examiner* — Matthew J Kasztejna
(74) *Attorney, Agent, or Firm* — Scully, Scott, Murphy & Presser, PC

(57) ABSTRACT

A video endoscope including: a endoscope shaft; a hermetically enclosed video-optical unit arranged in the endoscope shaft, wherein the video-optical unit comprises an enclosure including a substantially cylindrical, hermetically sealed housing having a distally arranged entry window, an objective lens, an image sensor unit, and one or more signal lines, the housing being connected to an outer jacket tube in a rotationally fixed manner, wherein the image sensor unit is mounted in the housing rotatably about a longitudinal axis of the endoscope shaft and comprises at least one image sensor, wherein, in order to rotate the image sensor unit, a magnetic coupling with an outer magnet and an inner magnet operationally connected to the outer magnet in a magnetic manner, is arranged in the area of the distal tip of the endoscope shaft.

13 Claims, 2 Drawing Sheets

(51) Int. Cl.
*A61B 1/00* (2006.01)
*G02B 23/24* (2006.01)

(52) U.S. Cl.
CPC ...... *A61B 1/00142* (2013.01); *A61B 1/00183* (2013.01); *A61B 1/051* (2013.01); *G02B 23/2423* (2013.01); *G02B 23/2484* (2013.01)

(56) References Cited

U.S. PATENT DOCUMENTS

| | | | |
|---|---|---|---|
| 5,797,836 A | 8/1998 | Lucey et al. | |
| 6,616,602 B1* | 9/2003 | Witte | G02B 23/2476 600/163 |
| 6,632,173 B1* | 10/2003 | Kehr | A61B 1/00188 348/E5.027 |
| 6,805,665 B1 | 10/2004 | Tatsuno et al. | |
| 7,278,965 B2 | 10/2007 | Shimizu | |
| 7,511,905 B2* | 3/2009 | Matsuki | A61B 1/00188 359/694 |
| 7,713,189 B2* | 5/2010 | Hanke | A61B 1/00183 600/109 |
| 8,803,957 B2* | 8/2014 | Makiyama | A61B 1/045 348/65 |
| 9,307,892 B2* | 4/2016 | Dahmen | A61B 1/00052 |
| 2006/0058581 A1 | 3/2006 | Hanke | |
| 2007/0010707 A1* | 1/2007 | Leiner | A61B 1/00126 600/112 |
| 2012/0182631 A1 | 7/2012 | Le et al. | |

FOREIGN PATENT DOCUMENTS

| | | |
|---|---|---|
| DE | 102011005255.0 | 3/2011 |
| DE | 102011078969.3 | 7/2011 |
| DE | 102010007394 A1 | 8/2011 |
| EP | 1759629 A1 | 3/2007 |
| EP | 1787570 A1 | 5/2007 |
| JP | S61-293439 A | 12/1986 |
| JP | 2002-153419 A | 5/2002 |
| JP | 2004-255083 A | 9/2004 |
| JP | 2005-329079 A | 12/2005 |
| WO | 96/39918 A1 | 12/1996 |
| WO | 2011/044878 A1 | 4/2011 |

OTHER PUBLICATIONS

English Abstract of EP 2353493 A1, dated Aug. 10, 2011.
Chinese Office Action dated Sep. 2, 2015 from related Chinese Patent Application No. 201280063568.7, together with an English language translation.

* cited by examiner

VIDEO ENDOSCOPE AND VIDEO ENDOSCOPE SYSTEM

CROSS-REFERENCE TO RELATED APPLICATION

The present application is a continuation of PCT/EP2012/005137 filed on Dec. 13, 2012, which is based upon and claims the benefit to DE 10 2011 090 132.9 filed on Dec. 29, 2011, the entire contents of each of which are incorporated herein by reference.

BACKGROUND

Field

The invention relates to a video endoscope, and in particular to a video endoscope having a longitudinally extended endoscope shaft, in which a hermetically enclosed video-optical unit is arranged, wherein the video-optical unit comprises an enclosure, particularly an at least substantially cylindrical, hermetically sealed housing as an enclosure, having a distally arranged entry window, an objective lens, an image sensor unit, and one or more signal lines, wherein the housing is connected to an outer jacket tube of the endoscope shaft in a rotationally fixed manner, and wherein the image sensor unit is mounted in the housing rotatably about a longitudinal axis of the endoscope shaft and comprises at least one image sensor, and a video endoscope system.

Prior Art

Video endoscopes are designed elongated with a small cross-section. In generic video endoscopes, image sensors and the upstream optical systems are normally arranged in the distal region of the endoscope shaft, that is, in the region of the endoscope tip. Image signals and control signals are transmitted via signal lines to or respectively from the proximal end, that is, the handle.

The autoclavability of the endoscope is a basic requirement. During autoclaving, the endoscope is treated with hot steam under high pressure. In the case of optical endoscopes and in particular video endoscopes, it is necessary to protect the optical components and the image sensor from steam which would otherwise condense on the optical system during cooling and impair the optical quality of the system. Video endoscopes are therefore normally constructed in a hermetically sealed manner. The hermetic seal prevents steam from penetrating into the hermetically sealed region. With conventional video optical systems, this normally extends from the shaft tip into the handle.

With optical systems having a sideways viewing direction, which can also be rotated about the longitudinal axis of the endoscope, a rotation of the image sensor to the sideways viewing optical system, for example a prism unit, and thus the jacket tube, is necessary. The rotation of these two optical components with respect to each other occurs in the hermetically sealed space. The image rotation is generated by the user in the handle of the optical system and must be transferred up to the tip. Thus, the seal must be guaranteed from the handle up to the tip of the video endoscope. As a result, the space in the jacket tube is limited and is utilized in order to implement a hermetically sealed unit, to transfer an image rotation, to transport light, and to guarantee a mechanically resilient design. Each of these different requirements must be satisfied, such that the optimization of one requirement occurs at the expense of another requirement.

Because there are endoscopes with different lengths of the endoscope shafts and jacket tubes, a suitable video-optical unit, i.e., the unit which comprises the optical system with objective lens and the image sensor, must be produced for each endoscope. A modular design with different lengths, which could also be different nationally, is therefore expensive.

SUMMARY

Based on this background, the object of the present invention is to provide a video-optical unit, a video endoscope and a video endoscope system that offer good autoclavability, good mechanical stability and high flexibility with low manufacturing costs.

This object is solved in a video endoscope with a longitudinally extended endoscope shaft, in which a hermetically enclosed video-optical unit is arranged, wherein the video-optical unit comprises an enclosure, particularly an at least substantially cylindrical, hermetically sealed housing as an enclosure, having a distally arranged entry window, an objective lens, an image sensor unit, and one or more signal lines, wherein the housing is connected to an outer jacket tube of the endoscope shaft in a rotationally fixed manner, wherein the image sensor unit is mounted in the housing rotatably about a longitudinal axis of the endoscope shaft and comprises at least one image sensor, in that a magnetic coupling with an outer ring magnet, or an outer magnet ring, and an inner ring magnet, or an inner magnet ring that is operationally connected to the outer ring magnet or magnet ring in a magnetic manner, is arranged in the area of a distal tip of the endoscope shaft in order to rotate the image sensor unit; wherein the inner ring magnet or magnet ring is arranged in the interior of the enclosure and connected to the image sensor unit, and the outer ring magnet or magnet ring is arranged outside of the enclosure and connected to a torsionally stiff carrier tube arranged outside of the enclosure, said carrier tube being rotatably mounted relative to a jacket tube of the endoscope and connected at a proximal end of the endoscope to a rotational device.

With the video endoscope according to the invention, the video-optical unit has a magnetic coupling for the rotation of the image sensor unit, if applicable advantageously also for the rotation of the objective lens. Here, the magnetic coupling has a ring magnet arranged outside of the housing of the video-optical unit and a ring magnet arranged within the housing, that is operationally connected to the outer ring magnet in a magnetic manner. Because the inner ring magnet is connected to the image sensor unit and/or to an adjustable part of a retainer of a sideways viewing optical assembly of the video-optical unit in a rotationally fixed manner, this enables a contactless control of the sideways viewing direction because for this purpose the hermetic seal of the housing of the video-optical unit does not need to be broken. Instead of ring magnets, magnetic rings can also be used, thus rings in which individual magnets are each enclosed or installed in the circumferential direction. Here, magnets of the outer magnet ring and the magnets of the inner magnet ring mutually attract each other.

The outer ring magnet or magnet ring is connected in the interior of the endoscope shaft via the carrier tube to a corresponding control part, or respectively a rotation apparatus, on the handle. The carrier tube is a rotatable tube located in the interior of the outermost jacket tube of the endoscope shaft. This can be designed to be stable and thus experience little torsion. Hereby it is possible to adjust the viewing direction very precisely.

The control at the handle can also occur using the magnetic coupling or an actuator. For this purpose the rotational device at the proximal end of the endoscope is preferably designed as a magnetic coupling. Appropriate ring magnets which can transmit a radial movement, however, if applicable also an axial movement, are known for example from the German patent application number 10 2011 078 969.3 from the applicant, the disclosed content of which shall be included in full in the present patent application by reference. The inner and outer ring magnets described therein, at the surfaces thereof, pointing toward each other, both in the axial direction as well as in the circumferential direction, have distributed pole shoes through which the magnetic flow is locally bundled between the outer and inner ring magnets, such that both radial as well as axial rotations and movements of the outer ring magnets are transmitted to the inner ring magnets and vice versa. Alternatively, the carrier tube is also accessible directly at the handle.

The video-optical unit of the video endoscope is preferably designed to be short and hermetically sealed. For this purpose the video-optical unit is preferably arranged in the area of a distal tip of the endoscope shaft, wherein the housing of the video-optical unit at the proximal end thereof has a hermetically sealed feed through of the housing through which the signal line(s) is/are guided into the endoscope shaft.

The housing preferably has a substantially cylindrical shape. The qualification of "substantially cylindrical" takes into account that the housing is adapted to be inserted into a jacket tube of an endoscope shaft and to be retained therein a form-locking and/or force-locking manner. If this retention occurs using a shrinking, the housing can also be designed completely cylindrical.

The video-optical unit comprises at least one entry window, an objective lens and an image sensor unit, as well as one or more signal lines, wherein the image sensor unit comprises at least one image sensor. If there are two image sensors, this can be a video-optical unit for a stereo video endoscope.

The video-optical unit according to the invention is short in comparison to the endoscope shaft, in particular less than half the length of the endoscope shaft. The remaining endoscope shaft does not need to be hermetically sealed. This allows the endoscope shaft to be built mechanically sturdier, for example with a greater wall thickness than previously possible. The support tube can also be designed sturdier and more torsion resistant than before, because due to the limited available space within the housing, the support tube previously had to be built thinner and with a smaller diameter than is possible according to the present invention.

Furthermore due to the use of the video-optical unit according to the invention it is possible to select any length and type of the endoscope shaft, for example to adapt to different endoscope types or requirements, wherein the endoscope shaft can be a rigid endoscope shaft or a flexible endoscope shaft. The video-optical unit can be manufactured as a stock item for example, and be installed in different length optical systems, whereby a modular building block-like design is possible. Furthermore, the assembly is simplified because the hermetically sealed video-optical unit is not produced only during the final assembly, rather is inserted prefabricated in its entirety into the endoscope shaft.

The proximal hermetically sealed feed through of the housing is produced preferably from a high-temperature multilayer ceramic (HTCC), a pressure molding, a hermetic molding, a soldered-in flat glass, a soldered connection and/or a weld connection.

In an advantageous development of the video-optical unit according to the invention, the video-optical unit has a 0° viewing direction, thus a straight view. Such a video-optical unit can be used advantageously in a video endoscope with rigid endoscope shaft, or alternatively also advantageously can be installed in a flexible video endoscope shaft so that a sideways viewing direction is adjusted by bending the endoscope shaft, or convoluted cavities can be examined endoscopically.

In an alternative development it is provided that the video-optical unit has a fixed, adjustable in steps, or steplessly adjustable sideways viewing direction, wherein the image sensor unit is mounted rotatably about the longitudinal axis of the video-optical unit. In this context, it is particularly advantageous if a deflecting prism with a fixed or adjustable viewing direction is arranged in the video-optical unit.

A video-optical unit with sideways viewing direction is preferably inserted in a video endoscope with rigid video endoscope shaft.

The magnetic coupling is advantageously designed additionally for the adjustment of a polar angle of a sideways viewing direction of the video-optical unit, wherein the inner ring magnet or magnet ring is connected to an adjustable part of a retainer of a sideways viewing optical assembly of the video-optical unit, and thus is mounted movable in an axial direction of the endoscope shaft. Such a magnetic coupling is described in the applicant's German patent application No. 10 2011 078 969.3.

The housing of the video-optical unit is advantageously adapted on the outside thereof, to be inserted and to be retained in an endoscope shaft of a video endoscope by form-locking and/or force-locking with appropriate retaining means of the endoscope shaft. The video-optical unit according to the invention is particularly easy to assemble in this manner. An example of form-locking, along with a threaded connection, can also be a bayonet connection or a snap connection. The form-lock can also be supplemented by a force-lock. If a cylindrical housing is inserted into a cylindrical endoscope shaft and clamped there by shrinkage of the shaft, this is also a combined form-lock and force-lock. The housing can also, if necessary, be soldered or bonded to the endoscope shaft or an integral bond can be attained in another manner. There can be orientation markings matched to each other, for instance a groove or spring or other suitable shapes in the endoscope shaft and on the housing thereof that ensure that the housing takes on a correct orientation.

The video-optical unit preferably has a viewing direction of 0°, and the endoscope shaft is designed bendable at least in a distal region. In this case the carrier tube is preferably designed bendable at least in sections, particularly as a spiral tube or having a spiral tube section.

Alternatively, the video-optical unit can also have a sideways viewing direction, which in particular can be set in steps or is steplessly changeable. Likewise, a rigid endoscope shaft can be used. The selection possibilities can be combined with each other according to requirement.

The video endoscope according to the invention can be produced at low cost. The parts to be protected during autoclaving are hermetically sealed and enclosed in the housing of the video-optical unit according to the invention. The video endoscope shaft can be built more rugged due to the space-saving because it does not need to be hermetically sealed over the entire length thereof.

Finally, the object of the invention is also solved by a video endoscope system having at least a video-optical unit of a previously described video endoscope according to the invention, and one or more endoscopes having rigid and/or bendable endoscope shafts, in which the at least one video-optical unit can be inserted for producing a previously described video endoscope according to the invention. A modular system is created in this manner, in which one or more different video-optical units with different specifications or different types can be combined flexibly with different video endoscope shafts of different lengths or different types. In this way, with an assembly kit of the video endoscope system according to the invention, a plurality of different video endoscopes according to the invention can be combined with little effort so that very different functionalities can be attained at low-cost, for which according to the prior art, a plurality of different endoscopes must be individually created. Likewise the manufacturer of the video endoscope can assemble the ordered video endoscopes as needed wherein the video endoscope can no longer be changed after production. This reduces the manufacturer's warehouse and production costs.

The advantages, properties, and features named for the individual invention objects, thus the video endoscope unit, the video endoscope and the video endoscope system, also apply without restriction to the respective other invention objects, which relate to, and build upon, each other.

Further characteristics of the invention will become apparent from the description of the embodiments according to the invention together with the claims and the included drawings. Embodiments according to the invention can fulfill individual characteristics or a combination of several characteristics.

BRIEF DESCRIPTION OF THE DRAWINGS

The invention is described below, without restricting the general idea of the invention, based on exemplary embodiments in reference to the drawings, whereby we expressly refer to the drawings with regard to the disclosure of all details according to the invention that are not explained in greater detail in the text. The figures show.

DETAILED DESCRIPTION

Figure 1:
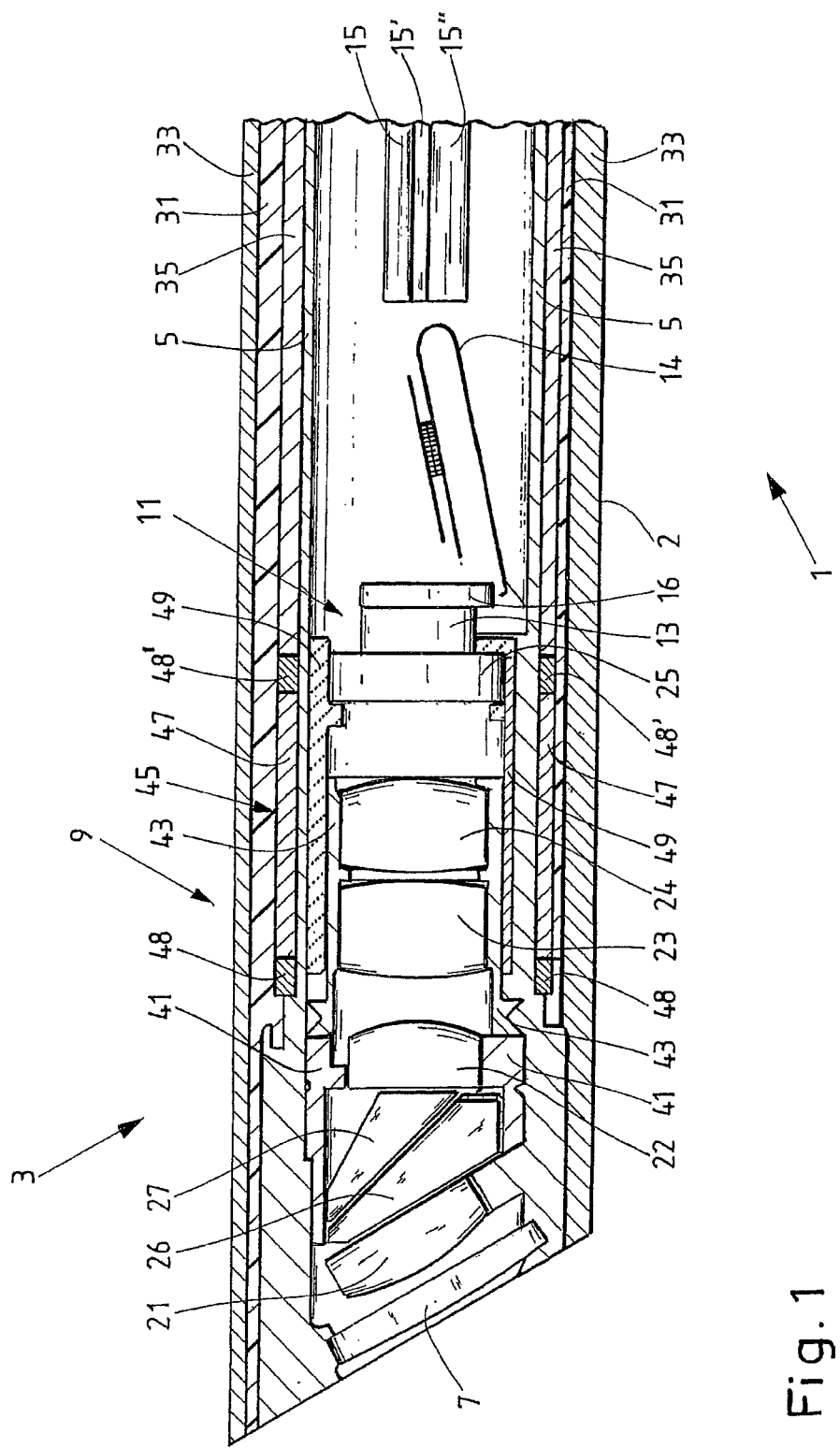
FIG. 1 illustrates a cross-section through the distal region of a video endoscope according to the invention.

In the drawings, the same or similar types of elements and/or parts are provided with the same reference numbers so that a corresponding re-introduction can be omitted.

FIG. 1 shows the distal tip of an endoscope shaft 2 of a video endoscope 1 according to the invention. The view contains a part of a video-optical unit 3 according to the invention. The video-optical unit 3 comprises a substantially cylindrical housing 5 that is somewhat expanded at the distal tip and is connected there in a form-locking manner to a fiber tube 31 and a jacket tube 33 of the endoscope shaft 2. The fiber tube 31 guides optical fibers (not shown) with which light for illuminating an operative field is conducted from the proximal end to the distal tip of the endoscope shaft 2.

At the distal tip of the housing 5 there is an entry window 7, made of sapphire glass for example, to which a system of lenses 21 to 24 connects, that reproduces the light entering through a cover window 25 onto an image sensor 13 of an image sensor unit 11. The lenses 21 to 24 form an objective lens 9.

Two partial prisms 26, 27, located between the lenses 21 and 22, together form a deflecting prism with which the light incident from a sideways direction is deflected onto the optical longitudinal axis of the housing 5 of the video-optical unit 3.

The image sensor 13 is connected to an evaluation and control electronics 16 that with a flexible signal line 14 guides signals proximally through signal lines 15, 15', 15".

The housing 5 of the video-optical unit 3 is arranged connected, in a rotationally fixed manner, in the jacket tube 33. This applies also for the entry window and the lens 21. The partial prisms 26, 27 are held by a prism holder 41, which also is connected, in a rotationally fixed manner, to the housing 5 of the video-optical unit 3. The prism holder 41 also serves as a holder for the lens 22.

The lenses 23 and 24 are held by an objective lens holder 43 which is mounted rotatably with respect to the housing 5 on an inner ring magnet 49 of a magnetic coupling 45, which also supports the image sensor unit 11. Thus, the image sensor unit 11 is mounted also rotatably with respect to the housing 5 and the endoscope shaft 2 as such.

The magnetic coupling 45 outside of the housing 5 has an outer ring magnet 47 with pole shoes 48, 48', opposite of which are pole shoes (not shown) of the inner ring magnet 49. A rotation of the outer ring magnet 47 therefore leads to a co-rotation of the inner ring magnet 49 and the objective lens holder 43 with the objective lens 23, 24, and the image sensor unit 11 with the image sensor 13. Instead of ring magnets 47, 49, magnet rings with several magnets can also be used.

The rear space in the interior of the housing 5 is hermetically sealed by a hermetic feed through not shown in FIG. 1.

The transfer of the rotation to the outer ring magnet 47 occurs by a carrier tube 35, which is mounted rotatably in the interior of the jacket tube 33 and the fiber tube 31, and is connected to an appropriate coupling in the handle.

Figure 2:
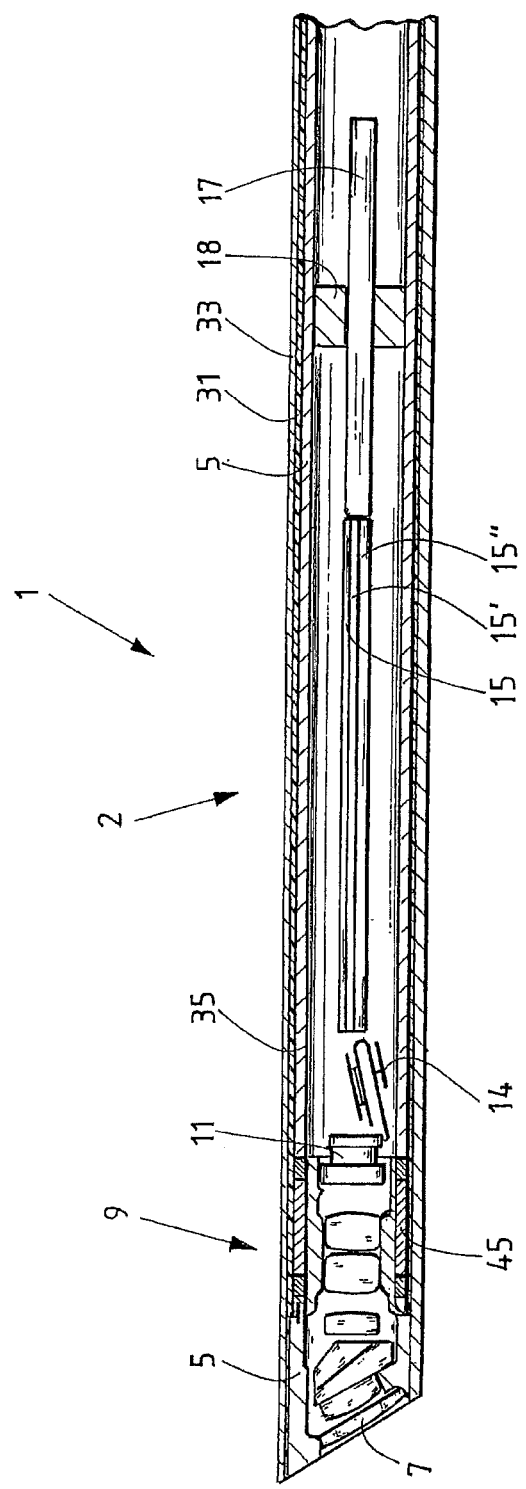
FIG. 2 illustrates a schematic overview of an endoscope shaft having a video-optical unit according to the invention.

FIG. 2 shows the video endoscope 1 from FIG. 1 in a view which comprises the entire video-optical unit 3. The distal elements are the same as shown in FIG. 1. In the proximal region of the video-optical unit 3 it is shown that the signal lines 15, 15', 15" transition into a line carrier 17 which is guided through a hermetic feed through 18. The hermetic feed through 18 closes the interior of the housing 5 of the video-optical unit 3 according to the invention, hermetically sealing both the outside as well as to the inside to the line carrier 17. The further progression of the line carrier, or respectively the line, is not shown in FIG. 2 for reasons of clarity. In addition, for clarity, details of the holders in the distal region of the video-optical unit 3 are partially not represented in FIG. 2.

Along with the example embodiments shown in FIGS. 1 and 2 having a fixed viewing direction, it is also possible to house a changeable sideways viewing direction in a video-optical unit according to the invention. Appropriate mechanics and actuator system for a viewing direction to be set in steps is known for example from the applicant's German patent application number 10 2011 005 255.0, the disclosure content of which shall be included in full in the present patent application by reference.

All named characteristics, including those taken from the drawings alone, and individual characteristics, which are disclosed in combination with other characteristics, are considered individually and in combination as essential to the invention. Embodiments according to the invention can be fulfilled through individual characteristics or a combination of several characteristics.

REFERENCE LIST 1 video endoscope
2 endoscope shaft
3 video-optical unit
5 housing
7 entry window
9 objective lens
11 image sensor unit
13 image sensor
14 flexible signal line
15-15" signal line
16 evaluation and control electronics
17 line support
18 hermetic feed through
21-24 lens
25 cover window
26, 27 partial prism
31 fiber tube
33 jacket tube
35 carrier tube
41 prism holder
43 objective lens holder
45 magnetic coupling
47 outer ring magnet
48, 48' pole shoe
49 inner ring magnet

What is claimed is:

1. A video endoscope comprising:
a longitudinally extended endoscope shaft;
a hermetically enclosed video-optical unit arranged in the endoscope shaft, wherein the video-optical unit comprises an enclosure, the enclosure including a hermetically sealed housing having a distally arranged entry window, an objective lens, an image sensor unit, and one or more signal lines, the housing being connected to an outer jacket tube of the endoscope shaft in a rotationally fixed manner, wherein the image sensor unit is mounted in the housing rotatably about a longitudinal axis of the endoscope shaft and comprises at least one image sensor,
wherein, in order to rotate the image sensor unit, a magnetic coupling with one of an outer ring magnet or an outer magnet ring and one of an inner ring magnet or an inner magnet ring that is operationally connected to the outer ring magnet or magnet ring in a magnetic manner, is arranged in the area of the distal tip of the endoscope shaft; and
the inner ring magnet or inner magnet ring is arranged in the interior of the enclosure and connected to the image sensor unit, and the outer ring magnet or outer magnet ring is arranged outside of the enclosure, and is connected to a torsionally stiff carrier tube arranged outside of the enclosure, said carrier tube being mounted rotatably relative to the outer jacket tube and connected at a proximal end to a rotational device.

2. The video endoscope according to claim 1, wherein the rotational device is configured as a magnetic coupling.

3. The video endoscope according to claim 1, wherein the video-optical unit is arranged in a region of a distal tip of the endoscope shaft, wherein the housing of the video-optical unit at the proximal end thereof has a feed through hermetically sealing the housing, through which the signal lines are led into the endoscope shaft.

4. The video endoscope according to claim 3, wherein the proximal hermetic feed through of the housing is produced from one of a high temperature multilayer ceramic, a pressure mold, a hermetic mold, a soldered planar glass, a solder connection or a weld connection.

5. The video endoscope according to claim 1, wherein the video-optical unit has one of a 0° viewing direction, a fixed sideways viewing direction or a sideways viewing direction adjustable in steps or steplessly adjustable.

6. The video endoscope according to claim 5, further comprising a deflection prism with one of a fixed or adjustable viewing direction arranged in the video-optical unit.

7. The video endoscope according to claim 5, wherein the magnetic coupling is configured for adjusting a polar angle of a sideways viewing direction of the video-optical unit, wherein the inner ring magnet or inner magnet ring is connected to an adjustable part of a retainer of a sideways viewing optical assembly of the video-optical unit.

8. The video endoscope according to claim 7, wherein the inner ring magnet or inner magnet ring is mounted movable in the axial direction of the endoscope shaft.

9. The video endoscope according to claim 1, wherein the housing of the video-optical unit is adapted at an outside thereof to be inserted and retained in the endoscope shaft by one of form-locking or force-locking with a retaining means of the endoscope shaft.

10. The video endoscope according to claim 1, wherein the video-optical unit has a viewing direction of 0°, and the endoscope shaft is bendable at least in a distal region.

11. The video endoscope according to claim 10, wherein the carrier tube is bendable at least in sections.

12. The video endoscope according to claim 1, wherein the housing is substantially cylindrical.

13. A video endoscope system having at least one video-optical unit of the video endoscope according to claim 1 and one or more endoscopes with rigid and/or bendable endoscope shafts, in which the at least one video-optical unit is inserted for producing the video endoscope of claim 1.

* * * * *